United States Patent [19]

O'Dowd

[11] Patent Number: 5,275,736
[45] Date of Patent: Jan. 4, 1994

[54] METHOD AMD DEVICE FOR PRODUCING PURE ELEMENTAL IODINE

[75] Inventor: Dennis H. O'Dowd, Toronto, Canada

[73] Assignee: Iomech Limited, Halifax, Canada

[21] Appl. No.: 842,153

[22] PCT Filed: Aug. 20, 1990

[86] PCT No.: PCT/CA90/00265
§ 371 Date: Mar. 27, 1992
§ 102(e) Date: Mar. 27, 1992

[87] PCT Pub. No.: WO91/04940
PCT Pub. Date: Apr. 18, 1991

[51] Int. Cl.[5] .............................................. B01D 61/24
[52] U.S. Cl. .................................... 210/638; 210/644
[58] Field of Search ............... 210/364, 638, 644, 640; 424/78.25, 427, 78.07, 78.17, 78.26

[56] References Cited

U.S. PATENT DOCUMENTS

| | | | |
|---|---|---|---|
| 2,984,623 | 5/1961 | Lee | 210/23 |
| 3,028,299 | 4/1962 | Winicov et al. | 167/17 |
| 3,028,300 | 4/1962 | Cantor et al. | 167/17 |
| 3,408,295 | 10/1968 | Uaichulis | 210/62 |
| 3,554,905 | 1/1971 | Place et al. | 210/644 X |
| 3,673,067 | 6/1972 | Harwood et al. | 210/644 X |
| 4,296,205 | 10/1981 | Verma | 210/644 X |
| 4,384,960 | 5/1983 | Polley | 210/753 |
| 4,555,347 | 11/1985 | O'Dowd et al. | 210/752 |
| 4,769,143 | 9/1988 | Deutch et al. | 210/266 |
| 4,816,255 | 3/1989 | Ghent | 424/150 |
| 4,996,048 | 2/1991 | Bhagwat et al. | 424/78.25 X |

FOREIGN PATENT DOCUMENTS 559167 9/1932 Fed. Rep. of Germany .
41703 3/1983 Japan .
148384 2/1961 U.S.S.R. .

OTHER PUBLICATIONS

Thrall and Bull-"Differences in the Distribution of Iodine and Iodide in the Sprague-Dawley Rat"-Fundamental and Applied Toxicology, 15, 75-81 (1990).
Schmidt and Winicov-"Detergent/Iodine Systems"-Soap and Chemical Specialties, Aug. 1967.

Primary Examiner—Frank Spear
Attorney, Agent, or Firm—Shlesinger Arkwright & Garvey

[57] ABSTRACT

A method and device for producing thermodynamically free iodine in which a source material containing thermodynamically free iodine is introduced to one side of an iodine solving solid barrier through which the thermodynamically free iodine passes by dispersion to the other side of the solid barrier until an equilibrium of thermodynamically free iodine vapor pressure is reached across the barrier. In a preferred embodiment of the invention, the degree to which the thermodynamically free iodine disperses to the other side of the iodine solving barrier may be controlled by means which reduce the vapor pressure of thermodynamically free iodine such as the variation of temperature of the iodine source material or of the other side of the barrier as well as the use of an iodine complexing compound or in combination with the source material.

48 Claims, 2 Drawing Sheets

METHOD AMD DEVICE FOR PRODUCING PURE ELEMENTAL IODINE

TECHNICAL FIELD

This invention relates to the production of pure elemental iodine.

BACKGROUND ART

Iodine (for example in the form of Lugol's solution or tincture of iodine) has long been recognized as an effective biocide. U.S. Pharmacopoeia and other similar publications in many countries have documented this property of iodine since 1830. Iodophores have been noted for their similar properties since 1960.

These iodines have been recognized for their bioactivity in man, animals, and in types of bacteria in plants and their seeds. In fact, a deficiency of iodine has been shown to prevent the attainment of maximum health, growth, and reproductive success.

It has been recently shown that the active component in all biocidal iodines is thermodynamically free iodine, which is uncomplexed or pure elemental iodine ($I_2$), as described in the Schmidt and Winicov article "Detergent/Iodine Systems" in Soap and Chemical Specialties, August 1967. It has also been recently shown that thermodynamically free iodine when fed to a mammal has a much decreased effect upon the thyroid compared to iodide, or iodine/iodide mixtures or mixtures of polyhalides (see Thrall and Bull in their article "Differences in the Distribution of Iodine and Iodide in the Sprague—Dawley Rat" in Fundamental and Applied Toxicology, 15, 75-81 (1990)).

The term thermodynamically free iodine describes iodine that is free from complexing. Thermodynamically free iodine in aqueous solution may dissociate into many hydrolyzed forms, depending upon concentration and/or pH, for example HIO (or also known as HOI), some of which are biocidal in nature. If a solution of aqueous iodine ($I_2$ +hydrolyzed biocidal forms where appropriate) could be reliably generated at any concentration of thermodynamically free iodine less than supersaturation, and remain stable at that level, it would allow the manufacture of many devices useful in water treatment, instrument sterilization, use as a source of nutritional iodine, plus other medicinal uses including the treatment of IDDs (Iodine Deficiency Disorders), chemical uses, and catalytic uses. For example, if a device could reliably produce a desired concentration of thermodynamically free iodine into a pH buffered fluid such that the thermodynamically free iodine remained unhydrolyzed and of known concentration despite moderate changes in ambient temperature, it would allow the treatment of many non-thyroidal IDDs and other medical conditions known to respond to treatment with iodine, such as in U.S. Pat. No. 4,816,255 of Ghent, with a much reduced toxicity (toxicity meaning thyroid complication found with other forms of iodine, iodides, iodine/iodide mixtures or polyhalides).

In an effort to produce biocidal iodine compounds, many methods, both chemical and mechanical in nature, have been devised. To date, however, these methods have had limited use and commercial success for reasons attributable to iodine's chemical and physical properties such as low solubility in $H_2O$, reactivity, easy contamination or the production of poly-halides and iodides and other potentially noxious adjuvants which inhibit the presence of thermodynamically free iodine, or its use in some applications.

Thermodynamically free iodine in all biocidal iodine solutions, whether alcohol/water, surfactant/water or other complexing agent/water, is confined to the water phase. Further, thermodynamically free iodine is usually found in solution in concentrations less than that of the total titratable iodine of the solution. For example, Lugol's solution, where potassium iodide (KI) is used to create a reservoir of iodine as $I_3^-$ through the relationship $I_2 + nI^- \rightleftharpoons I^- + I_n$, the solubility of elemental iodine is, increased to, for example, 1% (w/v); however, the amount of thermodynamically free iodine detectable is only circa 0.018% (w/v) or 180 ppm.

The germicidal capacity of these iodine formulations is dependent upon the continued release of thermodynamically free iodine from the reservoir of titratable iodine, as the thermodynamically free iodine in solution is depleted through dilution, contamination or biocidal activity. It has therefore been the goal of researchers to develop a practical means of creating this reservoir from which pure thermodynamically free iodine may be released alone, with no other adjuvants, into water in a controlled fashion.

Attempts have been made to develop a means to mechanically contain an amount of metallic elemental iodine in contact with water, as shown in U.S. Pat. No. 3,408,295 issued Oct. 29, 1968 in the name of John A. Vaichulis and in U.S. Pat. No. 4,384,960 issued May 24, 1983 in the name of Richard D. Polley. These methods, however, have not been totally effective in restraining micro-particles (and sometimes macro-particles) of iodine crystals from being carried away by the water flow. Further, these methods cannot prevent the contamination of the iodine reservoir by undesirable substances which may reduce the effectiveness of the reservoir, or facilitate the release of unwanted contaminants into the product stream containing the wanted thermodynamically free iodine and still further cannot provide stable levels of thermodynamically free iodine below the saturation level for iodine in a fluid in contact with the iodine.

Attempts have also been made to develop a chemical means of providing a reliable supply of thermodynamically free iodine. The chief fault of such systems (for example Lugol's solution, tincture of iodine, iodophores) is that a loss of solvent (i.e. water lost through evaporation) increases the total percentage of iodine in a volume and therefore, given iodine's relative insolubility, increases the toxic effect of the remaining solution (through recrystallization of elemental iodine) and subsequently reduces the availability of thermodynamically free iodine.

Another problem is that by chemical means, the level of thermodynamically free iodine in water is usually restricted to about 60% of the maximum solubility of thermodynamically free iodine in water (which is circa 0.03%). This is about 180 ppm (0.018%), and is usually found to be much less than that. For example, an iodophore of 3.75% titratable iodine may achieve maximum strength of less than 40 ppm of thermodynamically free iodine after dilution while having 75 ppm of titratable iodine. This discrepancy between the level of thermodynamically free iodine and the amount of titratable iodine makes the field testing for iodine concentration very cumbersome.

Where chemical adjuvants are used to increase the reservoir of titratable iodine, the adjuvants may act as an unwanted toxicant. There are many applications for the use of iodine in the medical field (i.e. the irrigation of wounds or incisions during surgery) and one adjuvant mixture used for this purpose was P.V.P.I. (poly(N-vinyl-2-pyrrolidone)-iodine). Eventually it was realized that the P.V.P. (poly(N-vinyl-2-pyrrolidone)) macro molecule tended to lodge in the lymph glands of a patient, causing problems with the function of the gland. This is one example of adjuvants causing undesirable side effects.

Finally, the thermodynamically free iodine should be as pure as practically and economically obtainable, for the end uses to which it is to be put. Any existing chemical means of releasing thermodynamically free iodine will likely release undesirable contaminants into the final product.

It is an object of the present invention to provide a reliable method of obtaining pure thermodynamically free iodine.

It is a further object of the invention to provide a device for obtaining pure thermodynamically free iodine.

It is a further object of this invention to show a method of, and a device for, obtaining thermodynamically free iodine in any predetermined concentration.

DISCLOSURE OF THE INVENTION

The invention consists of a method, and a device, for producing pure elemental iodine where a source containing thermodynamically free iodine is introduced on one side of a nonporous barrier impervious to solvents and contaminants of thermodynamically free iodine (hereinafter referred to as an iodine solving solid barrier), through which said thermodynamically free iodine passes by dispersion driven by vapour pressure differential between the two sides of the barrier until equilibrium of thermodynamically free iodine vapour pressure is reached across the barrier.

In a preferred embodiment of the invention, the degree to which the thermodynamically free iodine disperses to the other side of the iodine solving solid barrier may be controlled by means which reduce the vapour pressure of thermodynamically free iodine such as the variation of temperature of the iodine source material or of the other side of the barrier as well as the use of an iodine complexing compound in conjunction or in combination with the source material.

BRIEF DESCRIPTION OF DRAWINGS

Example embodiments of the drawings are shown in the accompanying drawings in which.

MODES FOR CARRYING OUT THE INVENTION

The diatomic molecule $I_2$, is only marginally soluble in water (circa 300 ppm). In many other fluids, iodine may form 2 distinct types of solution, which may be differentiated by their color (i.e. in organic solvents such as carbon tetrachloride, iodine imparts a violet color upon dissolution, whereas in water, a clear amber color is produced in the absence of polyhalides, complexing agents or other colorants. In the presence of polyhalides, a black color is produced). In these liquids, iodine exhibits a vapour pressure and also has a maximum solubility limit. In the presence of polyhalides and/or iodine complexing compounds, the iodine's vapour pressure is reduced.

Iodine also has the special property of being soluble in some solids. To iodine, these solids appear to behave as a liquid solvent (in the traditional sense of the properties of a liquid). When iodine is introduced to these solids, the solid is permeated by the iodine, imparting one of the two colors observed when iodine dissolves in liquids. In addition, over the solid, the iodine exhibits a vapour pressure and within the solid also has a solubility limit, both of which may be affected by complexing of $I_2$ either within the solid, or from the $I_2$ reservoir, or intermediate to the solid and reservoir.

Many of these special solids are impermeable to water and other solvents of iodine. Therefore should a solution containing a quantity of iodine be placed on one side of this solid barrier, and a solvent of iodine be placed on the other side of the solid barrier, the $I_2$ will move freely back and forth across the barrier until an equilibrium is reached. This equilibrium is reached when the chemical potential of iodine on either side of the barrier and over the barrier itself are equal. In addition, by choosing the appropriate thermodynamically free iodine donating source (i.e. iodine in combination or in conjunction with different types and concentrations of iodine complexing compounds) to control the vapour pressure over an iodine donating solution, the ultimate concentration on the other side of the barrier may be accurately controlled for a given temperature and solvent on the other side of the barrier, and even made stable irrespective of moderate temperature change of the donating source, barrier, or solvent on the other side of the barrier.

Also, by adjusting the temperature of the donating source, barrier, or solvent on the other side of the barrier, the vapour pressure of thermodynamically free iodine may be accurately controlled to provide a desired concentration ultimately reached on the other side of the barrier.

Figure 1:
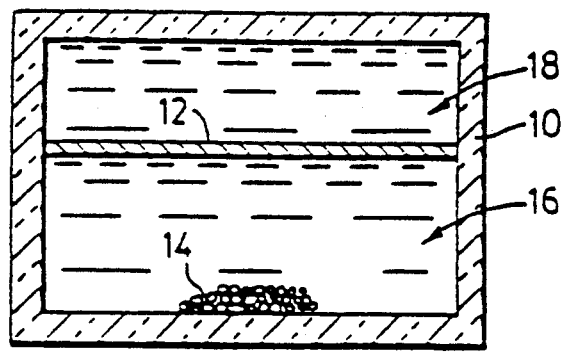
FIG. 1 is a schematic drawing showing a device for producing pure elemental iodine.

FIG. 1 of the drawings shows a container 10 which iodine molecules cannot penetrate, such as glass, a solid barrier 12 constructed from an iodine solving solid, a source of iodine 14 in chamber 16 containing a fluid and a second chamber 18 on the other side of barrier 12 containing a material into which the thermodynamically free iodine, diffusing through barrier 12, will pass until vapour pressure equilibrium is reached. Chamber 18 may be filled with a fluid such as water, be a vacuum chamber, be an iodine solving solid used to retain the thermodynamically free iodine, be an iodine complexing compound or adjuvant or other material to which one desires to expose a controlled amount of iodine.

One of the solid substances which exhibits this iodine solving property is polyethylene; both high and low density. It maybe preferable but not essential that the volume of the solving solid be low to reduce the quantity of iodine needed to achieve an equilibrium concentration, within the barrier, with respect to the final concentrations of the contents of the two chambers 16 and 18. For this reason, a low volume of iodine solving solid is preferred allowing rapid adjustment and equilibration of vapour pressure in all elements.

Figure 2:
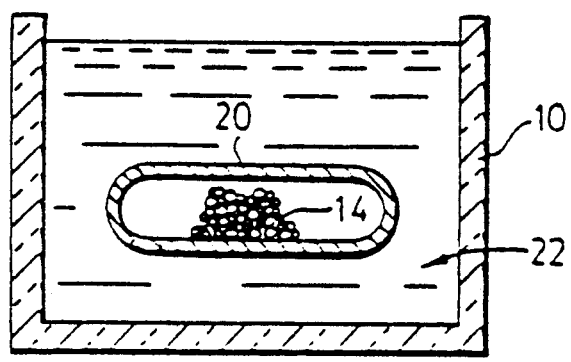
FIG. 2 is an alternate embodiment of FIG. 1.

FIG. 2 of the drawings shows an alternate arrangement of the components of FIG. 1 where the iodine solving solid 20 encapsulates the source quantity of iodine (i.e. water plus a quantity of thermodynamically free iodine donating material). The capsule would be capable of releasing a quantity of thermodynamically free iodine for the purposes of achieving a desired level of thermodynamically free iodine in the material contained in chamber 22. The encapsulation prevents direct physical contact by solvents or contaminants with the contents of the capsule. The encapsulating process should be effected using materials which add a minimum of iodine demand. The capsule may be formed as a rigid or non-rigid pillow. Upon being placed in chamber 22, capsule 20 will facilitate the transfer of $I_2$ molecules to the material in chamber 22 and will do so until the reservoir of iodine is depleted, or an equilibrium is attained between reservoir 14 and chamber 22. Once equilibrium is attained, should a quantity of thermodynamically free iodine in the reservoir 22 be lost due to biological action, complexing, or for some other reason, and therefore disrupt the thermodynamic balance, then more iodine will diffuse through the capsule wall 20 until equilibrium is once again attained.

Figure 3:
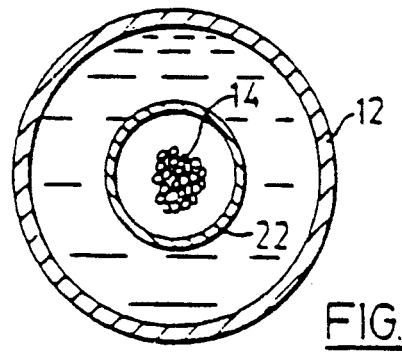
FIG. 3 is an alternate embodiment of FIG. 1.

FIG. 3 of the drawings shows an alternate construction in which the iodine solving solid barrier 12 is flexible and carries within it an iodine non-solving frangible container 22 containing iodine source 14. Use of this embodiment entails the squeezing of flexible barrier 12 in order to fracture the non-solving barrier 22 so that the source solution of iodine has access to the solving barrier. The entire construction is delivered to the material in which the thermodynamically free iodine, which subsequently diffuses through barrier 12, is required.

For this embodiment, an example of iodine source 14 material would be potassium iodide (KI) and a possible fluid surrounding frangible container 22 and confined by solid solving barrier 12 could be a water and chloramine mixture. When frangible container 22 is broken, the chemical reaction between the potassium iodide and chloramine would produce potassium chloride and thermodynamically free iodine (plus some free amines).

Figure 4:
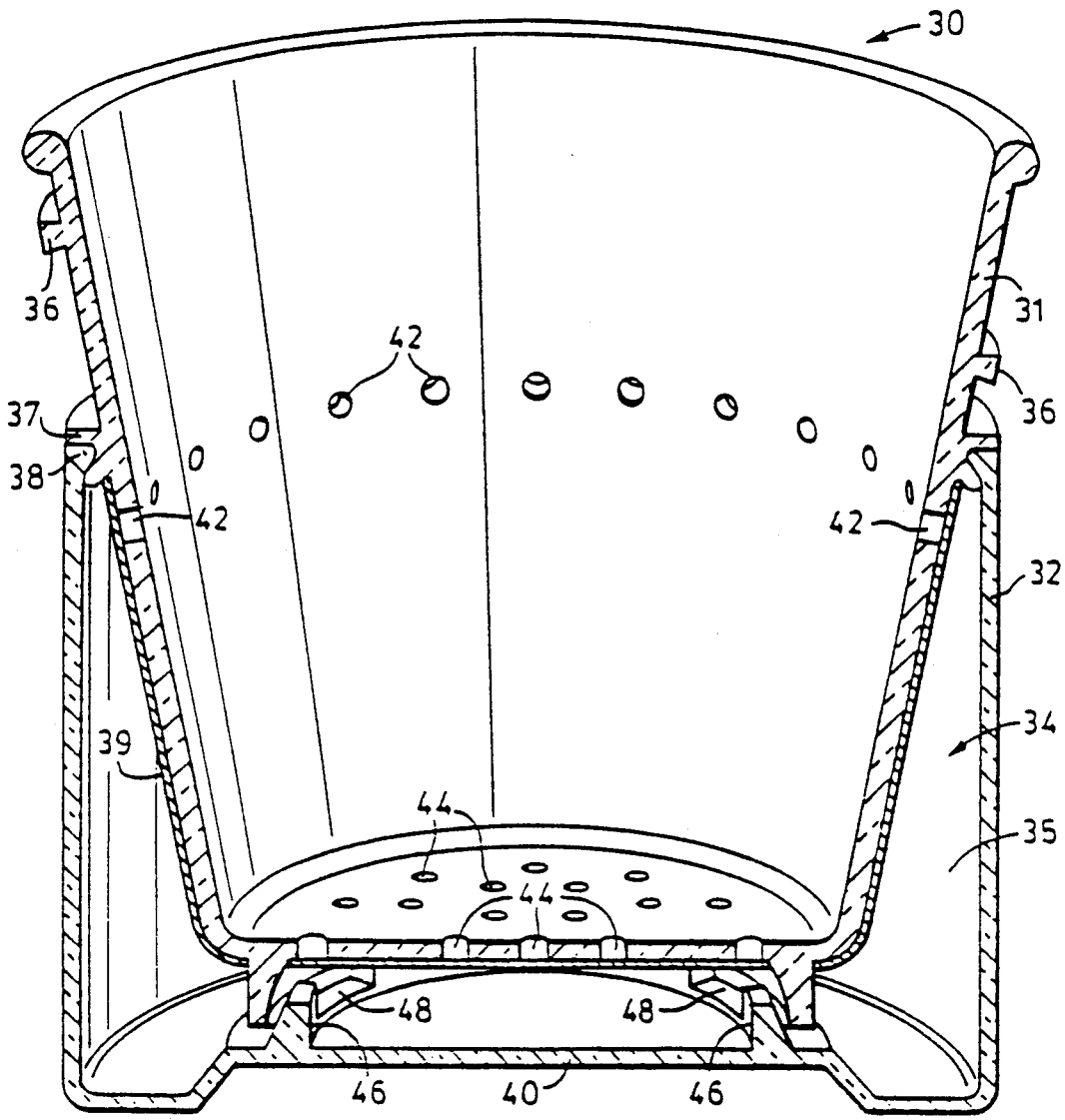
FIG. 4 is a cross-sectional view of an alternate embodiment of FIG. 1.

The device shown in FIG. 4 of the drawings consists of a unit 30 comprising a cup 31 which fits into a container 32, in a manner such that an annular cavity 34 is created between the two. Both cup 31 and container 32 are constructed of materials impenetrable to iodine (such as glass). A removable screw cap (not shown) fits on cup 31 by engaging a thread 36. Cup 31 has an annular flange 37 which seals onto rim 38 of container 32. The annular cavity 34 between cup 31 and container 32 is filled with an iodine source material 35 from which the thermodynamically free iodine will be extracted.

The outer surface of cup 31 below flange 37 is coated with an iodine solving solid layer 39. A ring of apertures 42 around cup 31 and a series of apertures 44 in the bottom of cup 31 exposes the contents of cup 31 to one surface of the iodine solving solid barrier 39. The bottom of cup 31 is spaced from the surface of container 32 by a ring flange 46 which has notches 48 spaced about its perimeter.

To disinfect a quantity of water, an amount of that water is poured into cup 31 approximately to the level of the apertures 42. The cap is then secured to cup 31 and the entire unit is shaken. The cap is removed and the water in the cup is now tinted brown with thermodynamically free iodine in solution. The tinted water may now be tested to determine the amount needed to disinfect the required quantity of water. This may be accomplished by dipping a piece of starched paper into the iodine containing water in cup 31, and comparing the shade of blue the strip changes to, with a standard color chart. Should an appropriate adjuvant/iodine mixture capable of complexing $I_2$ and reducing its vapour pressure be used for the thermodynamically free iodine donating material, then the concentration testing would not be necessary as a known concentration will exist in the product material.

This method and device have several advantages in that:

1) the iodine charged device has an indefinite shelf life;
2) the iodine cannot become contaminated;
3) as long as the source reservoir is not fully depleted, the contents of the cup will always achieve the same end concentration of thermodynamically free iodine regardless of the volume of water put into the cup;
4) a loss of water from the cup through processes such as evaporation will not increase the toxicity of the end solution, as the excess thermodynamically free iodine will merely diffuse back to the iodine source;
5) there is no need for the use of harmful adjuvants on the other (product) side of the solving barrier;
6) losses of thermodynamically free iodine on the other side of the solving barrier will be automatically replaced by thermodynamically free iodine diffusing from the source side of the solving barrier; and
7) when water is used on the other (product) side of the barrier, the resulting solution is unexpectedly non-toxic, non-irritating, non-burning to skin and mucosa, germicidal, and has an effect upon the thyroid which is less than 30% of the detrimental effect of other iodines, iodide mixtures, iodide/iodine mixtures, or polyhalides.

In each of the embodiments described, the iodine solving barrier may be constructed of, but is not restricted to, materials such as linear polyethylene, isotactic polyethylene, polyoxymethylene and polybutylene terephthalate. The barrier will be selected so as not to contribute detrimentally to the products final use.

Any of these iodine solving solid barriers may be impregnated with an iodine complexing compound to control the level of thermodynamically free iodine on the product side of the barrier. Examples of impregnating materials may be KI, NaI, and LiI.

In each embodiment, the thermodynamically free iodine source material may be a variety of compounds, including but not restricted to technical grade iodine which contains thermodynamically free iodine.

In each embodiment, iodine complexing compounds known to lower the maximum level of thermodynamically free iodine by complexing $I_2$ iodine and therefore lowering the vapour pressure of iodine over the iodine/complexing compound mixture, may be used to accurately control the equilibrium concentrations of thermodynamically free iodine on the other side of the barrier. This may be achieved by combining the iodine and complexing compound and using the mixture as the source of thermodynamically free iodine. Another method is to separate the iodine source from the iodine solving solid barrier with another like barrier, and placing the iodine complexing compound between the two. The effectiveness of the complexing compound can be varied with type and concentration. Examples of iodine complexing compounds are poly(N-vinyl-2-pyrrolidone), polyoxypropylene and nonyl phenol. A more extensive listing can be found in U.S. Pat. No. 3,028,299 by Winicov and Schmidt.

In each embodiment, the other side of the solid solving barrier, to which the thermodynamically free iodine from the source material is to diffuse, may contain a fluid (liquid or gas) or a solid. The fluid or solid may be either iodine-solvent or iodine-insolvent. The other side may also be a vacuum into which the thermodynamically free iodine would form an iodine vapour, whose concentration in the vacuum is controlled by the vapour pressure exerted by the iodine source. Further, the other side of the iodine solving solid barrier may contain an iodine complexing compound which would complex the thermodynamically free iodine which crosses the barrier.

In each embodiment, the temperature of the iodine source of the iodine solving solid barrier or of a material on the other side of the barrier may be adjusted to control the thermodynamically free iodine vapour pressure in that iodine source, iodine solving solid barrier or material on the other side of the barrier and by this means control the extent to which the thermodynamically free iodine passes through the barrier.

I claim:

1. A method for obtaining a desired amount of pure thermodynamically free iodine (TFI$_2$), comprising the steps of:
   (a) providing a TFI$_2$ solving solid barrier impervious to solvents and contaminants of TFI$_2$;
   (b) providing a source of TFI$_2$ which produces a predeterminable amount of TFI$_2$, the source of TFI$_2$ being located on one side of the solid barrier; and
   (c) providing a reservoir means on the other side of the solid barrier for receiving TFI$_2$ which passes through the barrier to establish an equilibrium of TFI$_2$ on both sides of the solid barrier, whereby there is a net flow of TFI$_2$ between both sides of the solid barrier in response to a nonequilibrium condition of TFI$_2$ on both sides of the solid barrier in order to reestablish the desired amount of TFI$_2$ on either side of the solid barrier.

2. A method as claimed in claim 1 in which the source of TFI$_2$ is encapsulated by the iodine solving solid barrier.

3. A method as claimed in claim 1 in which the thermodynamically free iodine is collected in a liquid.

4. A method as claimed in claim 3 in which said liquid is water.

5. A method as claimed in claim 1 in which the thermodynamically free iodine is collected in a gas.

6. A method as claimed in claim 1 in which said reservoir is a vacuum.

7. A method as claimed in claim 1 in which the thermodynamically free iodine is collected in an iodine solving solid.

8. A method as claimed in claim 1 in which the thermodynamically free iodine is collected on the surface of a solid in which iodine is not soluble.

9. A method as claimed in claim 1 in which the thermodynamically free iodine is collected in an iodine complexing compound.

10. A method as claimed in claim 9 in which the iodine complexing compound is selected from the class consisting of potassium iodide, sodium iodide, lithium iodide, poly(N-vinyl-2-pyrrolidone), polyoxypropylene and nonyl phenol.

11. A method as claimed in claim 1 in which the iodine source comprises an iodine/iodine complexing compound mixture, calibrated to reduce the vapour pressure of the thermodynamically free iodine by a predetermined amount.

12. A method as claimed in claim 11 in which the iodine complexing compound is selected from the class consisting of potassium iodide, sodium iodide, lithium iodide, poly(N-vinyl-2-pyrrolidone), polyoxypropylene and nonyl phenol.

13. A method as claimed in claim 1 in which the iodine source is separated from the iodine solving solid barrier by a further iodine solving solid barrier and an iodine complexing compound is provided between the two barriers.

14. A method as claimed in claim 13 in which the iodine complexing compound is selected from the class consisting of potassium iodide, sodium iodide, lithium iodide, poly(N-vinyl-2-pyrrolidone), polyoxypropylene and nonyl phenol.

15. A method as claimed in claim 1 in which the iodine solving barrier is a plastic.

16. A method as claimed in claim 15 in which the plastic is selected from the class consisting of linear polyethylene, isotactic polyethylene, polyoxymethylene and polybutylene terephthalate.

17. A method as claimed in claim 1 in which the iodine solving solid material is impregnated with an iodine complexing compound.

18. A method as claimed in claim 17 in which the impregnating material is selected from a class consisting of sodium iodide, potassium iodide, or lithium iodide.

19. A method as claimed in claim 1 in which the temperature is controllable in said source, said barrier or said other side of the barrier.

20. A device for producing a desired amount of pure thermodynamically free iodine (TFI$_2$), comprising:
   (a) a TFI$_2$ solving solid barrier impervious to solvents and contaminants if TFI$_2$;
   (b) a source of TFI$_2$ which produces a predetermined amount of TFI$_2$, the source located on one side of the solid barrier; and
   (c) a reservoir means located on the other side of the solid barrier for collecting TFI$_2$ which passes through the solid barrier to establish an equilibrium of TFI$_2$ on both sides of the solid barrier, whereby is a net flow of TFI$_2$ between both sides of the solid barrier in response to a nonequilibrium condition of TFI$_2$ on both sides of the solid barrier to reestablish the desired amount of TFI$_2$ on either side of the solid barrier.

21. A device as claimed in claim 20 in which the iodine source is encapsulated within the iodine solving solid barrier, and in which the means for collecting the thermodynamically free iodine is a container.

22. A device as claimed in claim 20 in which the means to collect the thermodynamically free iodine is a liquid.

23. A device as claimed in claim 22 in which said liquid is water.

24. A device as claimed in claim 20 in which the means for collecting the thermodynamically free iodine is a gas.

25. A device as claimed in claim 20 in which the product side of the iodine solving solid barrier consists of a vacuum.

26. A device as claimed in claim 20 in which the means to collect the thermodynamically free iodine is an iodine solving solid.

27. A device as claimed in claim 20 in which the thermodynamically free iodine is collected on the surface of a solid in which iodine is not soluble.

28. A device as claimed in claim 20 in which the thermodynamically free iodine is collected in an iodine complexing compound.

29. A device as claimed in claim 28 in which the iodine complexing compound is selected from the class consisting of potassium iodide, sodium iodide, lithium iodide, poly(N-vinyl-2-pyrrolidone), polyoxypropylene and nonyl phenol.

30. A device as claimed in claim 20 in which the iodine source consists of an iodine/iodine complexing compound mixture, calibrated to reduce the vapour pressure of thermodynamically free iodine by a predetermined amount.

31. A method as claimed in claim 30 in which the iodine complexing compound is selected from the class consisting of potassium iodide, sodium iodide, lithium iodide, poly(N-vinyl-2-pyrrolidone), polyoxypropylene and nonyl phenol.

32. A device as claimed in claim 20 in which the iodine source is separated from iodine solving solid barrier by a further iodine solving solid barrier and an iodine complexing compound is provided between the two barriers.

33. A device as claimed in claim 32 in which the iodine complexing compound is selected from the class consisting of potassium iodide, sodium iodide, lithium iodide, poly(N-vinyl-2-pyrrolidone), polyoxypropylene and nonyl phenol.

34. A device as claimed in claim 20 in which the iodine solving solid material is a plastic.

35. A device as claimed in claim 34 in which the iodine solving solid material is selected from a class consisting of linear polyethylene, isotactic polyethylene, polyoxymethylene and polybutylene terephthalate.

36. A device as claimed in claim 20 in which the iodine solving solid material is impregnated with an iodine complexing compound.

37. A device as claimed in claim 36 in which the impregnating material is selected from a class consisting of sodium iodide, potassium iodide and lithium iodide.

38. A device as claimed in claim 20 in which the temperature is controllable in said source, said barrier, or said other side of the barrier.

39. A device for producing a controlled amount of pure thermodynamically free iodine ($TFI_2$), comprising:
 (a) a container;
 (b) a cup opening from the container and defining a sealed cavity between the cup and the container;
 (c) a source of $TFI_2$ contained within the cavity; and
 (d) a $TFI_2$ solving solid barrier lining an outer wall of the cup located within the cavity, the cup being perforated adjacent the barrier lining, and the container and cup being formed of iodine impervious material.

40. A device as claimed in claim 39 in which the temperature is controllable in said source, said barrier, or said other side of the barrier.

41. A device as claimed in claim 39 in which the iodine source comprises an iodine/iodine complexing compound mixture, calibrated to reduce the vapour pressure of thermodynamically free iodine by a predetermined amount.

42. A device as claimed in claim 41 in which the iodine complexing compound is selected from the class consisting of potassium iodide, sodium iodide, lithium iodide, poly(N-vinyl-2-pyrrolidone), polyoxypropylene and nonyl phenol.

43. A device as claimed in claim 39 in which the iodine source is separated from the iodine solving solid barrier by a further iodine solving solid barrier and an iodine complexing compound is provided between the two barriers.

44. A device as claimed in claim 43 in which the iodine complexing compound is selected from the class consisting of potassium iodide, sodium iodide, lithium iodide, poly(N-vinyl-2-pyrrolidone), polyoxypropylene and nonyl phenol.

45. A device as claimed in claim 39 in which the iodine solving solid material is a plastic.

46. A device as claimed in claim 45 in which the iodine solving solid material is selected from a class consisting of linear polyethylene, isotactic polyethylene, polyoxymethylene and polybutylene terephthalate.

47. A device as claimed in claim 39 in which the iodine solving solid material is impregnated with an iodine complexing compound.

48. A device as claimed in claim 47 in which the impregnating material is selected from a class consisting of sodium iodide, potassium iodide and lithium iodide.

* * * * *